(12) United States Patent
Hayashi

(10) Patent No.: US 6,608,314 B1
(45) Date of Patent: Aug. 19, 2003

(54) METHOD AND APPARATUS FOR OBSERVATION USING QUANTUM DOTS

(75) Inventor: Shinichi Hayashi, Tokyo (JP)

(73) Assignee: Olympus Optical Co., Ltd., Tokyo (JP)

( * ) Notice: Subject to any disclaimer, the term of this patent is extended or adjusted under 35 U.S.C. 154(b) by 3 days.

(21) Appl. No.: 09/660,182

(22) Filed: Sep. 12, 2000

(30) Foreign Application Priority Data

Sep. 13, 1999 (JP) .......................................... 11-258373

(51) Int. Cl.[7] ................................................ G01J 1/22
(52) U.S. Cl. ................................ 250/458.1; 250/459.1
(58) Field of Search ........................ 250/458.1, 459.1, 250/352, 302, 303; 252/301.17; 257/614, 642; 356/317; 424/9.1; 428/402.24

(56) References Cited

U.S. PATENT DOCUMENTS

| | | | | |
|---|---|---|---|---|
| 5,891,016 A | * | 4/1999 | Utsui et al. | 600/181 |
| 6,114,038 A | * | 9/2000 | Castro et al. | 428/402.24 |
| 6,167,297 A | * | 12/2000 | Benaron | 600/431 |
| 6,333,110 B1 | * | 12/2001 | Barbera-Guillem | 428/402.24 |
| 2001/0055764 A1 | * | 12/2001 | Empedocles et al. | 435/6 |

OTHER PUBLICATIONS

Quantum Dot Bioconjugates for Ultrasensitive Nonisotopic Detection, Warren C. Chan et al, Sep. 25, 1998.vol. 281 Science, pp. 2016–2018 (Also see Appln. pp. 1, 2).

* cited by examiner

Primary Examiner—Constantine Hannaher
Assistant Examiner—Otilia Gabor
(74) Attorney, Agent, or Firm—Pillsbury Winthrop LLP

(57) ABSTRACT

The inventions relate to methods and systems suitable for sample observation using quantum dots. In an observation method wherein excitation light is applied to quantum dots, and light emitted from the quantum dots in a plurality of different wavelengths band is detected, the wavelength band of the excitation light is variably adjustable. An apparatus for carrying out the observation method includes a light source for producing excitation light to excite quantum dots, an illumination optical system for collecting and applying the excitation light to a sample containing the quantum dots, and a detection optical system for detecting light emitted from the quantum dots in a plurality of different wavelength bands. The illumination optical system has a variable filter device for adjusting the wavelength band of the excitation light.

16 Claims, 5 Drawing Sheets

METHOD AND APPARATUS FOR OBSERVATION USING QUANTUM DOTS

This application claims benefit of Japanese Application No. Hei 11-258373 filed in Japan on Sep. 13, 1999, the contents of which are incorporated by this reference.

BACKGROUND OF THE INVENTION

These inventions relate to methods and apparatus for observation using quantum dot. More particularly, they relate to emission observation methods using quantum dots and also relate to emission observation apparatus ofr carrying out the emissio observation methods.

Ultrahigh-sensitivity detecting machinery and materials recently developed have made it possible to detect and identify single molecules and to observe the motion thereof and have played an important role in analytical chemistry, molecular biology and the analysis of nanostructures.

In most conventional methods of observing single molecules, target molecules are labeled with fluorescent dyes and observed with a fluorescence miocroscope. However, as a substitute for the conventional methods, a method in which a sample is labeled with quantum dots has recently been proposed by W. C. W. Chan et al. (W. C. W. Chan and S. Nie, Science, vol. 281 (1998), p. 2016).

A typical example of quantum dot structures shown by W. C. W. Chan et al. is illustrated in FIG. 3. That is, the surface of a semiconductor CdSe microsphere with a diameter of 2 to 5 nanometers is coated with ZnS, and hydroxyl groups are adsorbed to the ZnS coating through sulfur molecules. One of the hydroxyl groups is coupled to a target protein.

In comparison to those of the conventional fluorescent dyes, as shown in FIG. 4, the emission characteristics of quantum dots have the following features. The half-width of the emission spectrum is about $\frac{1}{20}$ of the center wavelength, which is as narrow as about $\frac{1}{3}$ of that of fluorescent dyes. The peak wavelength of the emission spectrum can be set relatively freely within a range of from about 400 nanometers to about 2000 nanometers by selecting a size and material of quantum dots. Further, the excitation spectrum increases in intensity as the wavelength becomes shorter in the visible to ultraviolet regions irrespective of the position of the center wavelength of the emission spectrum. FIG. 4 shows excitation and emission spectral distributions of quantum dots of CdSe and InP that are different in particle diameter from each other.

When used for single-molecule detection, quantum dots have the following advantages in comparison to conventional fluorescent dyes of organic substances. One of the advantages is that the size is very small so that the quantum dots can hardly interfere with the motion of the target molecule. Another advantage is that the emission efficiency is much higher than that of the conventional fluorescent dyes, and it is therefore possible to detect single molecules with high sensitivity. Another advantage is that the toxicity is very low; therefore, in vivo observation can be performed. Still another advantage is that fading can hardly occur. In view of these advantages, quantum dots are expected to be widely used in future analyses using the technique of single-molecule detection in place of the conventional fluorescent dyes.

In simultaneous identification of a plurality of different kinds of molecules, quantum dots have the following advantages in comparison to the conventional fluorescent dyes. With quantum dots, a plurality of emission center wavelengths can be set relatively freely by selecting a particle size and a material as has been stated above. Moreover, the half-width of the emission spectrum is narrow. Therefore, it is possible to identify a larger number of different kinds of molecules than in the case of the conventional method using fluorescent dyes in a usable wavelength band. Further, in the case of quantum dots, the excitation spectrum increases in excitation intensity as the wavelength becomes shorter in the visible region irrespective of the position of the center wavelength of the emission spectrum. Therefore, it is possible to efficiently excite all quantum dots in a single wavelength band.

Incidentally, an ordinary incident light fluorescence microscope can be used to identify a plurality of different kinds of substances labeled with quantum dots.

An ordinary incident light fluorescence microscope has the following optical elements: an excitation filter for selecting a wavelength band for excitation of a fluorescent dye used; a barrier filter that blocks light in the transmission wavelength band of the excitation filter and passes light in the fluorescence wavelength band; and a dichroic mirror that reflects light in the transmission wavelength band of the excitation filter and passes light in the fluorescence wavelength band. Light from a light source passes through the excitation filter to become excitation light limited to a predetermined wavelength band. The excitation light is reflected by the dichroic mirror toward a sample in a coaxial relation to an observation light path to illuminate the sample. Fluorescence from the sample excited by the excitation light travels along the observation light path in the opposite direction to the excitation light and passes through the dichroic mirror. The barrier filter blocks the residual component of the excitation light in the light passing through the dichroic mirror and passes the fluorescent light. By using these three optical elements, it is possible to produce fluorescence by excitation light and to detect fluorescent light, which is feeble in comparison to the excitation light, with high contrast.

In the ordinary incident light fluorescence microscope, the above-described three optical elements are integrated into a fluorescence cube, and a multiplicity of fluorescence cubes adapted for the emission characteristics of various fluorescent dyes are prepared. The fluorescence cubes are often arranged to be switched from one to another by a simple operation according to each particular fluorescent dye used. For example, there is a publicly known incident light fluorescence microscope arrangement in which a plurality of fluorescence cubes are placed on a turret so that the fluorescence cubes can be switched from one to another simply by rotating the turret. There is also a known arrangement in which a plurality of fluorescence cubes are placed on a slider so as to be switchable from one to another simply by sliding the slider.

To observe a sample labeled with a plurality of quantum dots different in size or material from each other by using such an incident light fluorescence microscope, the wavelength characteristics of the three optical elements should be set as shown in FIG. 5. That is, the excitation filter blocks light of longer wavelength than the minimum value $\lambda_0$ in the emission band of quantum dots used and passes light of shorter wavelength than the minimum value $\lambda_0$. The barrier filter blocks light of shorter wavelength than $\lambda_0$ and passes light of longer wavelength than $\lambda_0$. The dichroic mirror reflects light of shorter wavelength than $\lambda_0$ and passes light of longer wavelength than $\lambda_0$. By setting the wavelength characteristics of the three optical elements as stated above, feeble light emitted from quantum dots can be observed with high contrast without being superimposed on the intense excitation light.

It is preferable from the viewpoint of detection efficiency to prepare a plurality of fluorescence cubes different in $\lambda_0$ and to arrange them to be switchable from one to another freely according to the emission band of quantum dots used.

Incidentally, when an ordinary incident light fluorescence microscope is used to detect a sample labeled with quantum dots, the following problems arise:

If it is intended to excite quantum dots efficiently and increase the intensity of light emitted from the quantum dots so as to detect the light with high contrast, it is preferable that the wavelength region of excitation light that is shorter than $\lambda_0$ should be widened as much as possible. However, the short-wavelength component of excitation light may cause autofluorescence to occur from an encapsulating medium fixing the sample and also from a vitreous material constituting the objective lens. The autofluorescence may cause the contrast of the observation image to be reduced remarkably. Because the degree of autofluorescence varies according to the encapsulating medium and the objective lens material, it is not preferable to preset an excitation wavelength band. That is, if an excitation wavelength band is set at a certain value in advance, the emission efficiency of quantum dots will not be optimized when a sample and an objective lens that can hardly emit autofluorescence are used. In particular, when extremely feeble light is to be detected as in single-molecule observation, the detection capability will be reduced remarkably. In addition, $\lambda_0$ for the detection of such extremely feeble light may vary according to the sample and the objective lens used.

SUMMARY OF THE INVENTION

In view of the above-described problems with the prior art, the inventions described/claimed herein provide methods and systems suitable for the observation of quantum dots.

The inventions provide observation methods wherein excitation light is applied to quantum dots, and light emitted from the quantum dots in a plurality of different wavelength bands is detected. The wavelength band of the excitation light is variably adjustable.

According to these inventions, the wavelength band of excitation light is adjusted according to the characteristics of autofluorescence that may occur in an optical system used, thereby allowing the quantum dot excitation efficiency to be maximized within a range in which the fluorescence observation is not affected by the autofluorescence. Therefore, the observation method is particularly suitable for the detection of feeble light as in single-molecule observation.

Other features and advantages of the inventions will be apparent from the specification.

The inventions accordingly comprise the features of construction, combinations of elements, and arrangement of parts which will be exemplified in the construction hereinafter set forth, and the scope of the inventions will be indicated in the claims.

DETAILED DESCRIPTION

Figure 1:
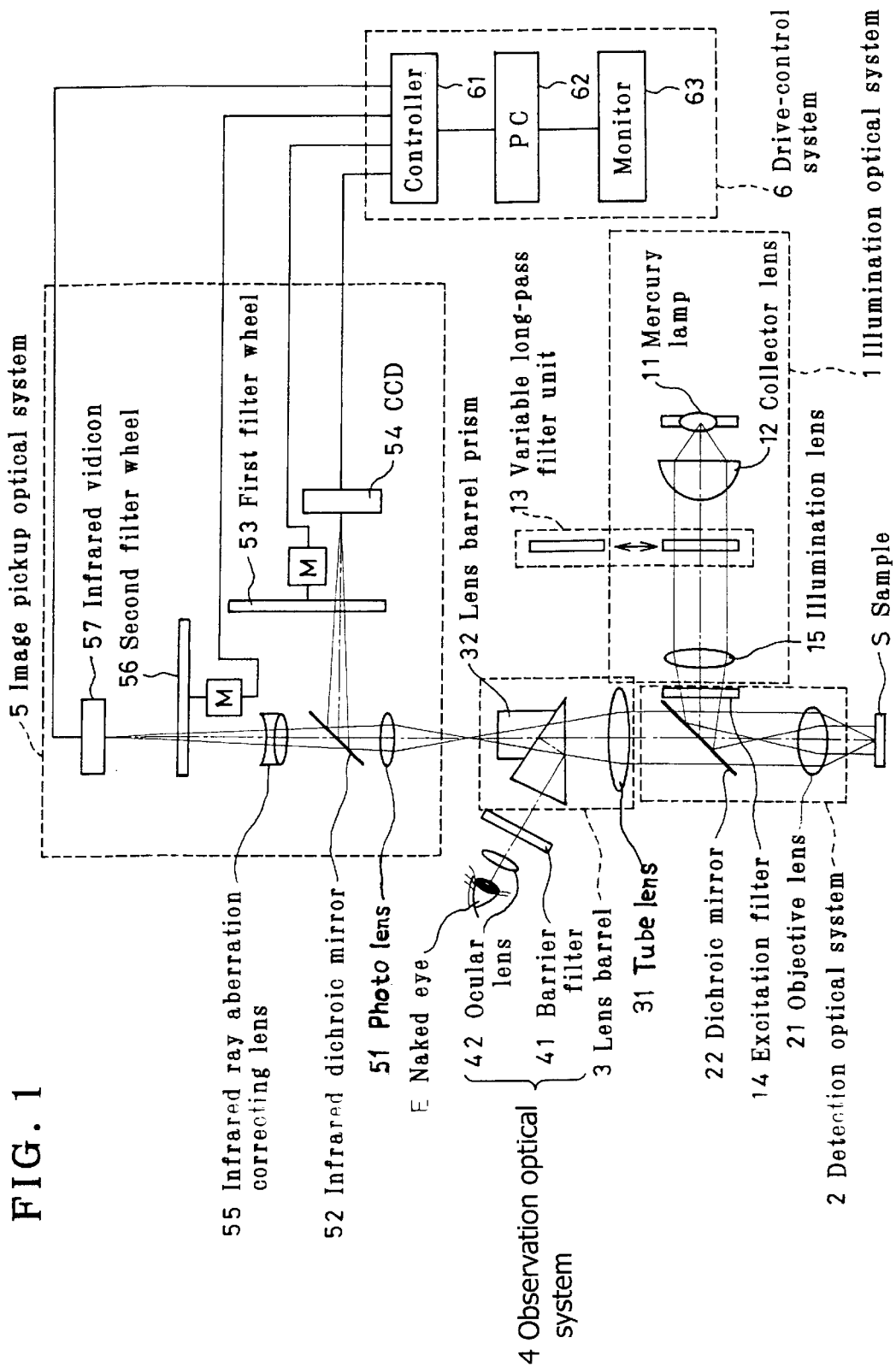
FIG. 1 is a diagram showing the arrangement of an observation apparatus using quantum dots according to an embodiment of the present invention.

In a preferred embodiment of the inventions, the wavelength band of excitation light can be adjusted with a simple system arrangement by using a variable filter device whose spectral transmittance is adjustable as a method of adjusting the wavelength band of excitation light.

In a preferred embodiment of the inventions, the variable filter device may have a plurality of filters having the property of a long-pass filter or a short-pass filter in the wavelength band of excitation light and different in cut-off wavelength from each other. If these filters are selectively used, the wavelength band of excitation light can be readily adjusted simply by switching the filters from one to another.

If the variable filter device is an interference filter having the property of a long-pass filter or a short-pass filter in the wavelength band of excitation light and arranged so that the tilt thereof with respect to the optical axis is adjustable, the wavelength band of excitation light can be readily adjusted simply by adjusting the tilt of the interference filter.

Alternatively, the variable filter device may be a liquid crystal tuneable filter. In this case, the wavelength band of excitation light can be readily adjusted simply by varying the voltage applied to the liquid crystal tuneable filter.

Alternatively, the emission wavelength band of a light source for producing excitation light may be adjusted as a method of adjusting the wavelength band of excitation light. By doing so, the wavelength band of excitation light can be adjusted with a simple system arrangement.

If a multi-wavelength laser is used as the light source, the wavelength band of excitation light can be readily adjusted by varying the electric current applied to the multi-wavelength laser.

In addition, the inventions provide an observation apparatus including a light source for producing excitation light to excite quantum dots. An illumination optical system collects excitation light from the light source and applies the collected excitation light to a sample containing the quantum dots. A detection optical system detects light emitted from the quantum dots in a plurality of different wavelength bands. The illumination optical system has a variable filter device for adjusting the wavelength band of the excitation light.

According to the arrangement of the apparatus of the present invention, the wavelength band of excitation light is adjusted with the variable filter device according to the characteristics of autofluorescence that may occur in the optical system used, thereby allowing the quantum dot excitation efficiency to be maximized within a range in which the fluorescence observation is not affected by the autofluorescence. Therefore, it is possible to provide an apparatus particularly suitable for the detection of feeble light as in single-molecule observation.

If the variable filter device has a plurality of filters having the property of a long-pass filter or a short-pass filter in the wavelength band of excitation light and different in cut-off wavelength from each other, it is possible to provide an apparatus that allows the wavelength band of excitation light to be adjusted with a simple system arrangement.

Alternatively, the variable filter device may have an interference filter having the property of a long-pass filter or a short-pass filter in the wavelength band of excitation light and arranged so that the tilt thereof with respect to the optical axis is adjustable. In this case, it is possible to provide an apparatus that allows the wavelength band of excitation light to be readily adjusted simply by adjusting the tilt of the interference filter.

Alternatively, the variable filter device may have a liquid crystal tuneable filter. In this case, it is possible to provide an apparatus that allows the wavelength band of excitation light to be readily adjusted simply by varying the voltage applied to the liquid crystal tuneable filter.

In addition, the inventions provide an observation apparatus including a light source for producing excitation light to excite quantum dots. An illumination optical system collects excitation light from the light source and applies the collected excitation light to a sample containing the quantum dots. A detection optical system detects light emitted from the quantum dots in a plurality of different wavelength bands. The light source has a device for adjusting the wavelength band of light produced therefrom.

According to the arrangement of the apparatus of the inventions, the wavelength band of excitation light is adjusted with the wavelength band adjusting device provided in the light source according to the characteristics of autofluorescence that may occur in the optical system, thereby allowing the quantum dot excitation efficiency to be maximized within a range in which the fluorescence observation is not affected by the auto fluorescence. Therefore, it is possible to provide an apparatus particularly suitable for the detection of feeble light as in single-molecule observation.

If a multi-wavelength laser is used as the light source, it is possible to provide an apparatus that allows the wavelength band of excitation light to be readily adjusted by varying the electric current applied to the multi-wavelength laser.

In addition, the inventions provide an observation apparatus including a light source for producing excitation light to excite quantum dots. An illumination optical system applies the excitation light to a sample containing the quantum dots. A condenser optical system collects light emitted from the quantum dots. An observation optical system is arranged to observe the light emitted from the quantum dots with the naked eye. The observation apparatus further includes an image pickup optical system for detecting the light emitted from the quantum dots to perform imaging. The illumination optical system includes a variable long-pass filter unit in which a cut-off wavelength for determining the lower limit of the wavelength band of the excitation light to be applied to the quantum dots is variable. The illumination optical system further includes an excitation filter formed from a short-pass filter having a cut-off wavelength for determining the upper limit of the wavelength band of the excitation light to be applied to the quantum dots. The observation optical system includes a barrier filter formed from a short-cut filter for cutting off the excitation light. The image pickup optical system includes a plurality of filter devices different in transmission wavelength band for setting a plurality of different transmission wavelength bands.

According to an arrangement of the apparatus of the inventions, the lower limit of the excitation light wavelength band is adjusted with the variable long-pass filter unit according to the characteristics of autofluorescence that may occur in the optical system, thereby allowing the quantum dot excitation efficiency to be maximized within a range in which the fluorescence observation is not affected by the autofluorescence. In addition, the quantum dots different in emission wavelength band can be imaged separately from each other by detecting light emitted from the quantum dots while changing imaging wavelength regions from one to another with the filter devices in the image pickup optical system. Moreover, the image pickup optical system does not contain a barrier filter. Therefore, it is possible to provide an apparatus particularly suitable for the detection of feeble light for imaging as in single-molecule observation.

In addition, the inventions provide an observation apparatus including a light source for producing excitation light to excite quantum dots. An illumination optical system applies the excitation light to a sample containing the quantum dots. A condenser optical system collects light emitted from the quantum dots. An observation optical system is arranged to observe the light emitted from the quantum dots with the naked eye. The observation apparatus further includes an image pickup optical system for detecting the light emitted from the quantum dots to perform imaging. The illumination optical system includes a long-pass filter unit having a cut-off wavelength for determining the lower limit of the wavelength band of the excitation light to be applied to the quantum dots. The illumination optical system further includes a variable excitation filter formed from a short-pass filter in which a cut-off wavelength for determining the upper limit of the wavelength band of the excitation light to be applied to the quantum dots is variable. The observation optical system includes a barrier filter formed from a short-cut filter for cutting off the excitation light. The image pickup optical system includes a plurality of filter devices different in transmission wavelength band and capable of setting a plurality of different transmission wavelength bands.

According to the arrangement of the apparatus of the inventions, the upper limit of the excitation light wavelength band is adjusted with the variable excitation filter according to the emission band characteristics of the quantum dots used, thereby allowing the quantum dot excitation efficiency to be maximized within a range in which the reduction in contrast due to crosstalk is inconspicuous. In addition, the quantum dots different in emission wavelength band can be imaged separately from each other by detecting light emitted from the quantum dots while changing imaging wavelength regions from one to another with the filter devices in the image pickup optical system. Moreover, the image pickup optical system does not contain a barrier filter. Therefore, it is possible to provide an apparatus particularly suitable for the detection of feeble light for imaging as in single-molecule observation.

In addition, the inventions provide an observation apparatus including a light source for producing excitation light to excite quantum dots. An illumination optical system applies the excitation light to a sample containing the quantum dots. A condenser optical system collects light emitted from the quantum dots. An observation optical system is arranged to observe the light emitted from the quantum dots with the naked eye. The observation apparatus further includes an image pickup optical system for detecting the light emitted from the quantum dots to perform imaging. The illumination optical system includes a variable long-pass filter unit in which a cut-off wavelength for determining the lower limit of the wavelength band of the excitation light to be applied to the quantum dots is variable. The illumination optical system further includes a variable excitation filter formed from a short-pass filter in which a cut-off wavelength for determining the upper limit of the wavelength band of the excitation light to be applied to the quantum dots is variable. The observation optical system includes a barrier filter formed from a short-cut filter for cutting off the excitation light. The image pickup optical system includes a plurality of filter devices different in transmission wavelength band and capable of setting a plurality of different transmission wavelength bands.

According to the arrangement of the apparatus of the inventions, the lower limit of the wavelength band of the excitation light is adjusted with the variable long-pass filter unit according to the characteristics of autofluorescence that may occur in the optical system, and further, the upper limit of the excitation light wavelength band is adjusted with the variable excitation filter according to the emission band characteristics of the quantum dots used, thereby allowing the quantum dot excitation efficiency to be maximized within a range in which the fluorescence observation is not affected by the autofluorescence and crosstalk. In addition, the quantum dots different in emission wavelength band can be imaged separately from each other by detecting light emitted from the quantum dots while changing imaging wavelength regions from one to another with the filter devices in the image pickup optical system. Moreover, the image pickup optical system does not contain a barrier filter. Therefore, it is possible to provide an apparatus particularly suitable for the detection of feeble light for imaging as in single-molecule observation.

An embodiment of an observation apparatus for carrying out the observation method using quantum dots according to the present invention will be described below with reference to the accompanying drawings.

As shown in FIG. 1, an observation apparatus according to an embodiment of the inventions include an illumination optical system 1. The illumination optical system 1 has a mercury lamp 11, a collector lens 12, a variable long-pass filter unit 13, an excitation filter 14, and an illumination lens 15. The variable long-pass filter unit 13 includes a plurality of long-pass filters different in cut-off wavelength, which can be selectively loaded onto and unloaded from an optical axis. The observation apparatus further includes a detection optical system 2 having an objective lens 21 and a dichroic mirror 22. Further, a lens barrel 3 includes a tube lens 31 and a lens barrel prism 32. An observation optical system 4 includes a barrier filter 41 and an ocular lens 42. An image pickup optical system 5 includes a photo lens 51, an infrared dichroic mirror 52, a first filter wheel 53, a CCD 54, an infrared ray aberration correcting lens 55, a second filter wheel 56, and an infrared vidicon 57. A drive-control system 6 includes a controller 61, a personal computer (PC) 62, and a monitor 63.

Illuminating light emitted from the mercury lamp 11 is collimated through the collector lens 12. The short wavelength-side cut-off wavelength of excitation light is adjusted by a variable long-pass filter in the variable long-pass filter unit 13. Then, the light is converged toward the pupil position of the objective lens 21 by the illumination lens 15. The excitation filter 14 blocks light components in the emission spectral bands of quantum dots used. Then, the light is deflected so as to travel along the optical axis of the objective lens 21 by the dichroic mirror 22 and applied to a sample S through the objective lens 21 with a uniform intensity over the entire field. Light emitted from the quantum dots on the sample S is collected by the objective lens 21. After passing through the dichroic mirror 22, the light from the quantum dots is passed through the tube lens 31 to form a sample image in the lens barrel 3. After the residual component of the excitation light has been removed by the barrier filter 41, the sample image thus formed is observed with the naked eye E through the ocular lens 42. It is also possible to capture a fluorescence image by re-forming a sample image on the image pickup surface of the CCD 54 and that of the infrared vidicon 57 through the photo lens 51.

In this embodiment, the barrier filter 41, which is conventionally provided in the lens barrel 3, is placed in the observation optical system 4, thereby preventing lowering in intensity of a quantum dot image captured by the image pickup optical system 5, which would otherwise be caused by the barrier filter 41. Thus, feeble light from the quantum dots can be detected efficiently to perform imaging.

The infrared dichroic mirror 52 is placed on the optical axis connecting the photo lens 51 and the image pickup surface of the infrared vidicon 57. The infrared dichroic mirror 52 reflects light components in the visible to near infrared regions and passes infrared light. The infrared ray aberration correcting lens 55 is placed on the optical axis connecting the infrared dichroic mirror 52 and the image pickup surface of the infrared vidicon 57. The infrared ray aberration correcting lens 55 corrects aberrations introduced into the infrared light component of the sample image and performs magnification conversion in conformity to the resolution of the infrared vidicon 57. The first filter wheel 53 is placed on the optical axis connecting the infrared dichroic mirror 52 and the image pickup surface of the CCD 54. The second filter wheel 56 is placed on the optical axis connecting the infrared ray aberration correcting lens 55 and the infrared vidicon 57. The first and second filter wheels 53 and 56 each have a plurality of filters with different spectral transmittances which can be selectively loaded onto and unloaded from the optical axis so that quantum dots having respective emission spectra can be distinguished from each other. The operation of loading and unloading each filter is carried out by a motor connected to the PC 62 through the controller 61. The emission spectrum of each quantum dot can be identified by computing with the PC 62 using the image intensity obtained when each filter is used. Thus, the kind of a molecule labeled with the quantum dot can be identified.

Figure 2:
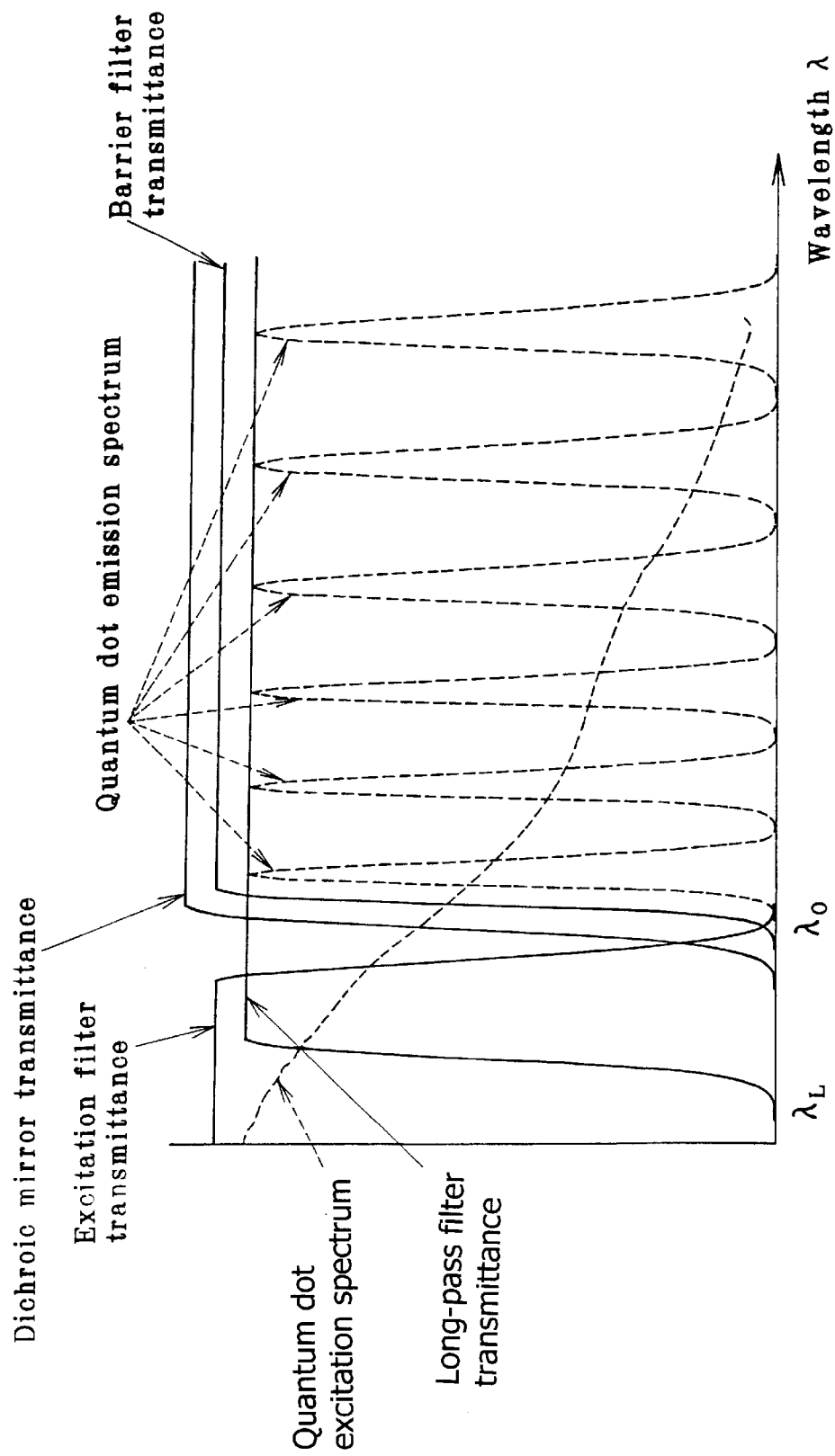
FIG. 2 is a diagram illustrating wavelength characteristics of optical elements of the observation apparatus using quantum dots shown in FIG. 1.
Figure 3:
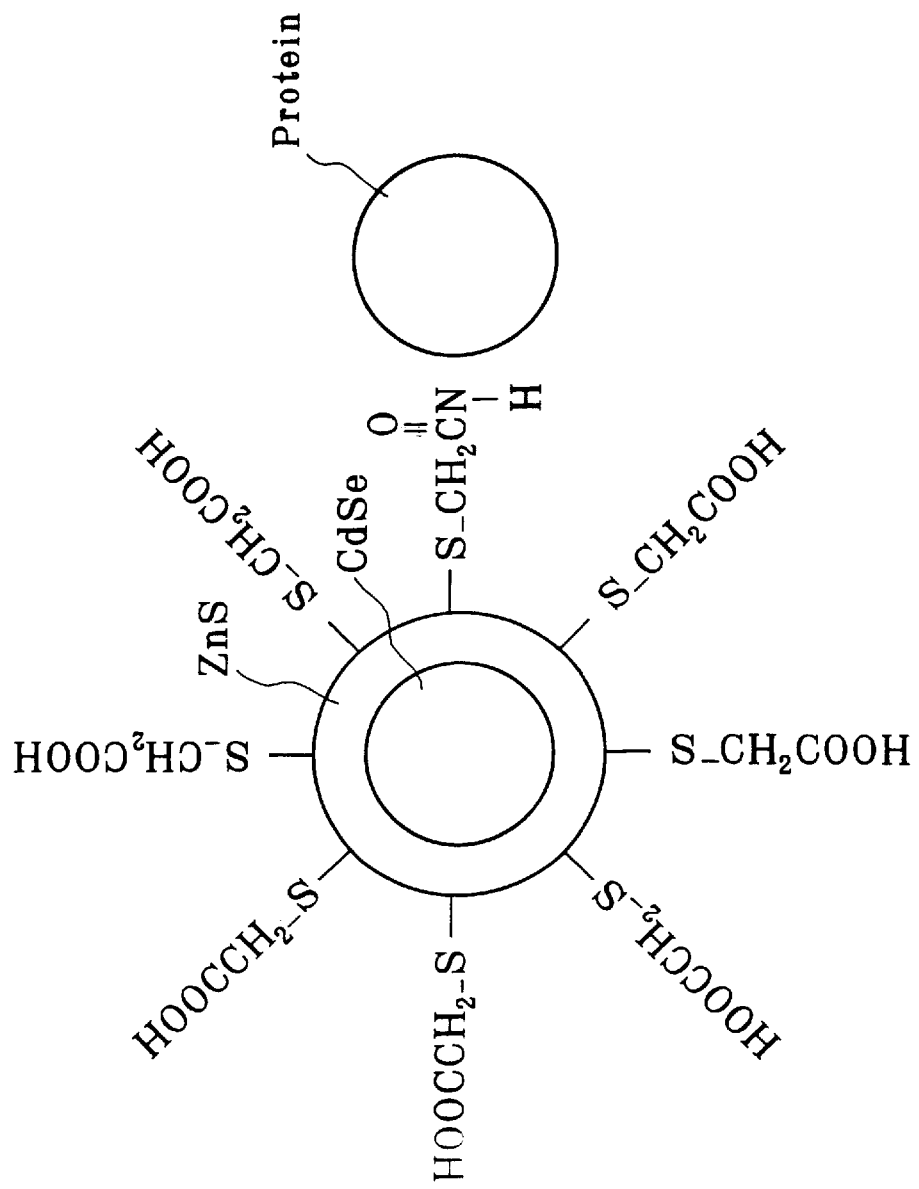
FIG. 3 is a diagram showing a typical example of quantum dot structures.
Figure 4:
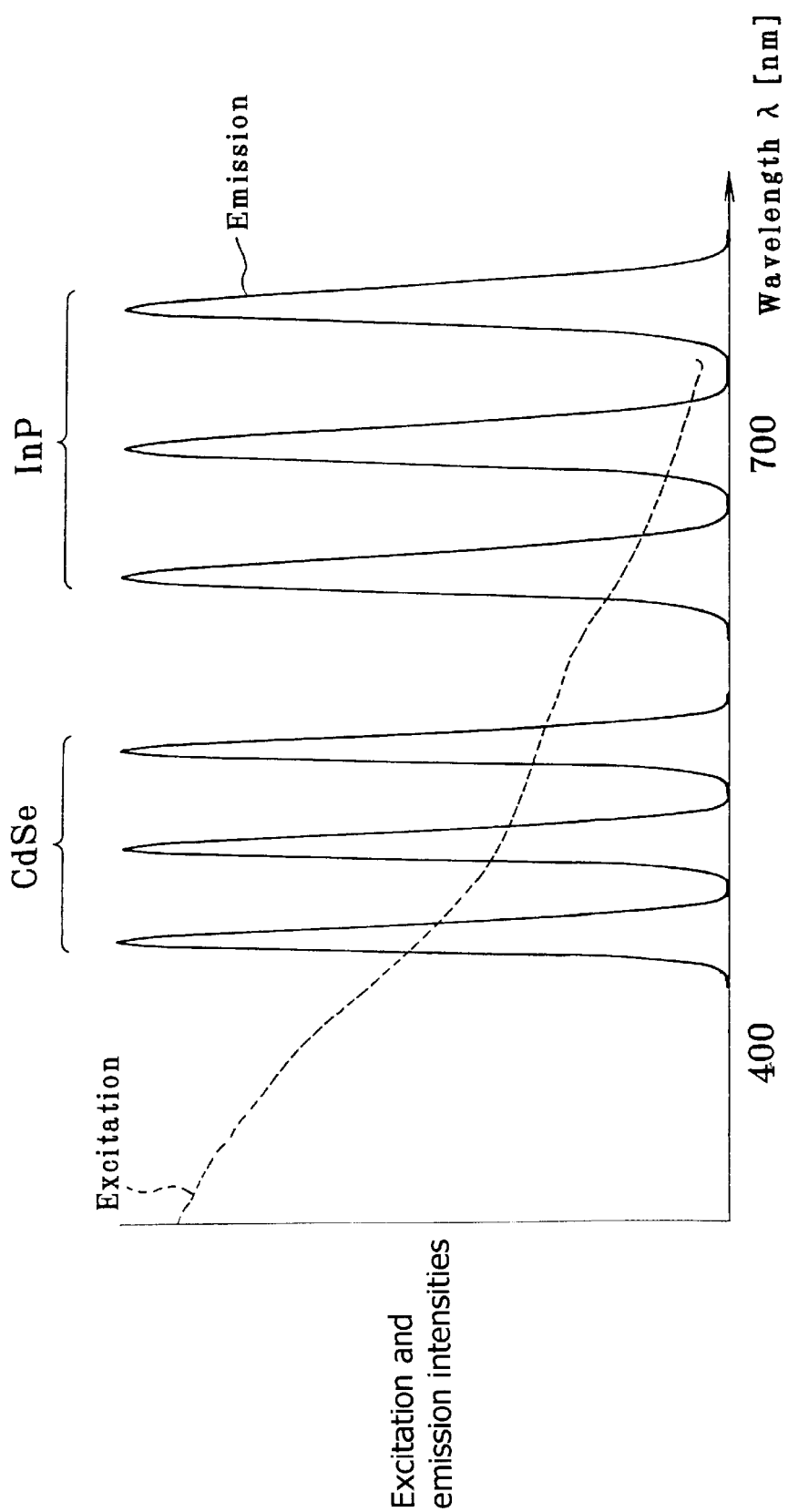
FIG. 4 is a diagram illustrating excitation and emission spectra of quantum dots.
Figure 5:
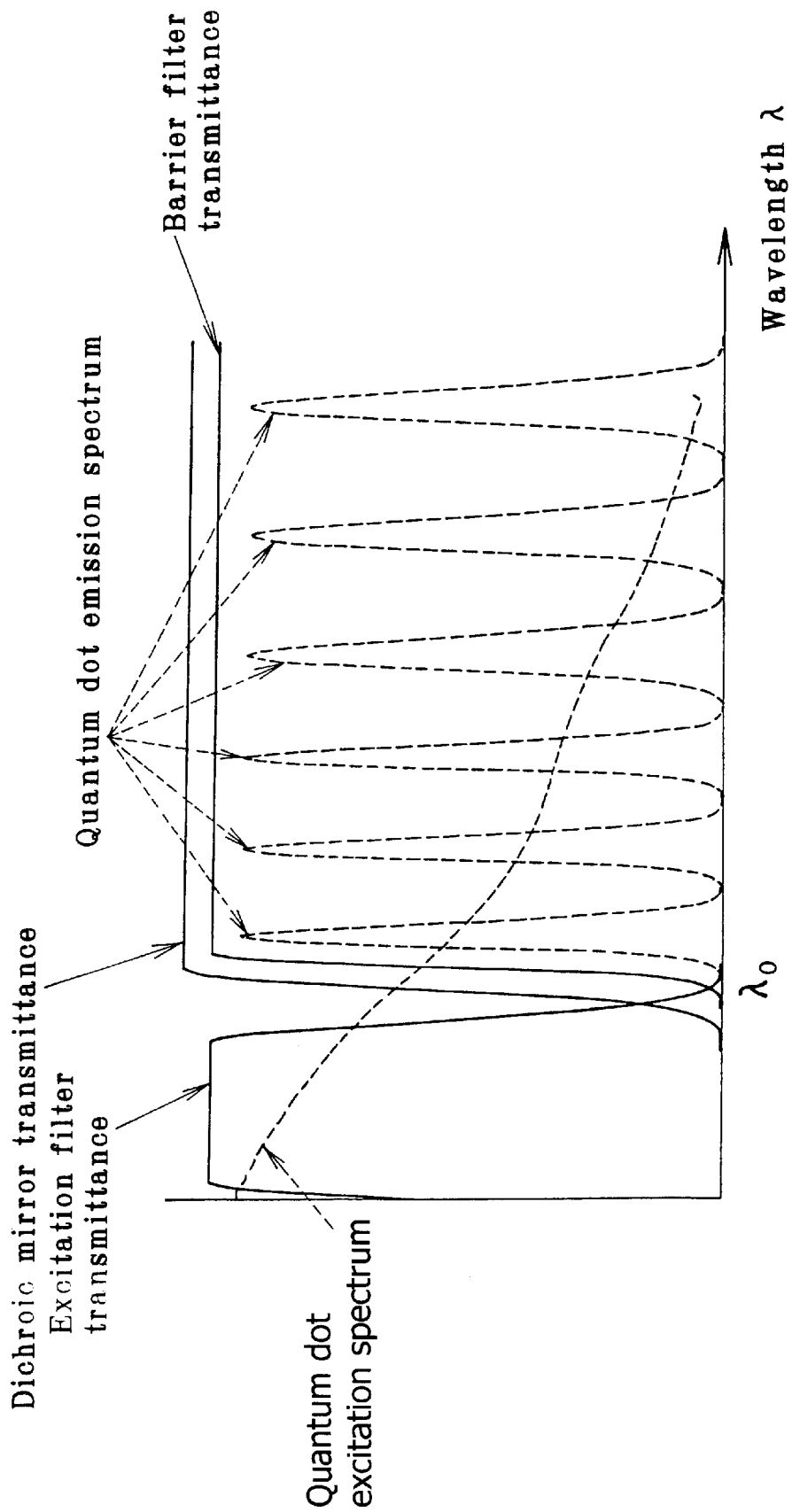
FIG. 5 (Prior Art) is a diagram illustrating wavelength characteristics of optical elements of a conventional incident light fluorescence microscope.

The variable long-pass filter unit 13 is arranged such that a plurality of long-pass filters different in cut-off wavelength can be selectively inserted into a position on the optical axis of the illumination optical system 1. Thus, the cut-off wavelength on the short wavelength side of excitation light can be adjusted easily. The spectral characteristics of each long-pass filter are as shown in FIG. 2. That is, a wavelength $\lambda_L$ shorter than the emission wavelength band $\lambda_0$ of a quantum dot is defined as a cut-off wavelength of a long-pass filter. Consequently, the long-pass filter blocks light of shorter wavelength than $\lambda_L$ and passes wavelengths longer than $\lambda_L$. The cut-off wavelength $\lambda_L$ differs for each long-pass filter. By adjusting the short wavelength-side cut-off wavelength of excitation light with the variable long-pass filter unit 13, it is possible to adjust the intensity of autofluorescence, which is harmful to feeble light detection such as single-molecule detection. Autofluorescence is likely to occur more strongly as the wavelength of excitation light becomes shorter. Therefore, the intensity of autofluorescence weakens if the short wavelength component of excitation light is cut off. However, cutting off the short wavelength component of excitation light also affects the intensity of light emitted from the quantum dots. For this reason, the optimum cut-off wavelength is determined by trade-off between the reduction in intensity of autofluorescence and the intensification of light emitted from the quantum dots. It is desirable to adjust the cut-off wavelength while viewing the object under observation.

The excitation filter 14 and the dichroic mirror 22 are integrally formed in conformity to the optical characteristics thereof. It is desirable that the combination of the excitation filter 14 and the dichroic mirror 22 should be switched to another according to the emission spectrum (short wavelength side) of quantum dots used. By doing so, the spectral width of excitation light can be widened as much as possible, and hence the intensity of light emitted from the quantum dots can be increased favorably.

The observation apparatus according to this embodiment can be realized by simple remodeling that merely requires adding the image pickup optical system 5 and the variable long-pass filter unit 13 to an ordinary incident light fluorescence microscope and moving the barrier filter 41 to a position immediately in front of or behind the ocular lens 42.

In place of the variable long-pass filter unit in this embodiment, a long-pass filter formed from an interference layer may be provided on the optical axis of the illumination optical system 1 such that the angle of the filter with respect to the optical axis is adjustable. Filters formed from an interference layer generally have the property that the wavelength characteristics vary according to the incident angle of rays. In this case, the cut-off wavelength of the long-pass filter shifts with the change in the incident angle of rays. Accordingly, the excitation light wavelength band can be finely and continuously adjusted.

In place of the variable long-pass filter unit in this embodiment, a liquid crystal tuneable filter may be disposed in the same position. The liquid crystal tuneable filter allows the transmission wavelength band to be shifted continuously by varying the voltage applied thereto. Therefore, the excitation light wavelength band can be finely and continuously adjusted under computer control.

As will be clear from the foregoing description, the observation method using quantum dots according to the present invention makes it possible to detect extremely feeble light with high sensitivity, for example, in the observation of single molecules stained with quantum dots.

In addition, the inventions make it possible to provide an observation apparatus capable of detecting extremely feeble light with high sensitivity with a simple system arrangement, which is particularly suitable for use in the observation of single molecules stained with quantum dots.

What we claim is:

1. An observation method using quantum dots, comprising:

applying excitation light to the quantum dots, detecting light emitted from the quantum dots in a plurality of different wavelength bands, and adjusting variably a wavelength band of said excitation light to maximize excitation efficiency.

2. An observation method using quantum dots according to claim 1, wherein variable filter means whose spectral transmittance is adjustable is used as a means for adjusting the wavelength band of said excitation light.

3. An observation method using quantum dots according to claim 2, wherein a plurality of filters having a property of either a long-pass filter or a short-pass filter in the wavelength band of said excitation light and different in cut-off wavelength from each other are selectively used as said variable filter means.

4. An observation method using quantum dots according to claim 2, wherein an interference filter having a property of either a long-pass filter or a short-pass filter in the wavelength band of said excitation light and arranged so that a tilt thereof with respect to an optical axis is adjustable is used as said variable filter means.

5. An observation method using quantum dots according to claim 2, wherein a liquid crystal tuneable filter is used as said variable filter means.

6. An observation method using quantum dots according to claim 1, wherein an emission wavelength band of a light source for producing said excitation light is adjusted as a means for adjusting the wavelength band of said excitation light.

7. An observation method using quantum dots according to claim 6, wherein a multi-wavelength laser is used as said light source.

8. An observation apparatus comprising:

a light source for producing excitation light to excite quantum dots;

an illumination optical system for collecting excitation light from said light source and for applying the collected excitation light to a sample containing said quantum dots; and a detection optical system for detecting light emitted from said quantum dots in a plurality of different wavelength bands;

wherein said illumination optical system has variable filter means for adjusting a wavelength band of said excitation light.

9. An observation apparatus according to claim 8, wherein said variable filter means has a plurality of filters having a property of either a long-pass filter or a short-pass filter in the wavelength band of said excitation light and different in cut-off wavelength from each other.

10. An observation apparatus according to claim 8, wherein said variable filter means has an interference filter having a property of either a long-pass filter or a short-pass filter in the wavelength band of said excitation light and arranged so that a tilt thereof with respect to an optical axis is adjustable.

11. An observation apparatus according to claim 8, wherein said variable filter means has a liquid crystal tuneable filter.

12. An observation apparatus comprising:

a light source for producing\excitation light to excite quantum dots;

an illumination optical system for collecting excitation light from said light source and for applying the collected excitation light to a sample containing said quantum dots; and a detection optical system for detecting light emitted from said quantum dots in a plurality of different wavelength bands;

wherein said light source has means for adjusting a wavelength band of light produced therefrom.

13. An observation apparatus according to claim 12, wherein said light source is a multi-wavelength laser.

14. An observation apparatus comprising:

a light source for producing excitation light to excite quantum dots;

an illumination optical system for applying said excitation light to a sample containing said quantum dots;

a condenser optical system for collecting light emitted from said quantum dots;

an observation optical system for observing the light emitted from said quantum dots with a naked eye; and an image pickup optical system for detecting the light emitted from said quantum dots to perform imaging;

wherein said illumination optical system includes:

a variable long-pass filter unit in which a cut-off wavelength for determining a lower limit of a wavelength band of said excitation light to be applied to said quantum dots is variable; and an excitation filter formed from a short-pass filter having a cut-off wavelength for determining an upper limit of the wavelength band of said excitation light to be applied to said quantum dots;

said observation optical system including a barrier filter formed from a short-cut filter for cutting off the excitation light;

said image pickup optical system including a plurality of filter devices different in transmission wavelength band for setting a plurality of different transmission wavelength bands.

15. An observation apparatus comprising:

a light source for producing excitation light to excite quantum dots;

an illumination optical system for applying said excitation light to a sample containing said quantum dots;

a condenser optical system for collecting light emitted from said quantum dots;

an observation optical system for observing the light emitted from said quantum dots with a naked eye; and an image pickup optical system for detecting the light emitted from said quantum dots to perform imaging;

wherein said illumination optical system includes:

a long-pass filter unit having a cut-off wavelength for determining a lower limit of a wavelength band of said excitation light to be applied to said quantum dots; and a variable excitation filter formed from a short-pass filter in which a cut-off wavelength for determining an upper limit of the wavelength band of said excitation light to be applied to said quantum dots is variable;

said observation optical system including a barrier filter formed from a short-cut filter for cutting off the excitation light;

said image pickup optical system including a plurality of filter devices different in transmission wavelength band and capable of setting a plurality of different transmission wavelength bands.

16. An observation apparatus comprising:

a light source for producing excitation light to excite quantum dots;

an illumination optical system for applying said excitation light to a sample containing said quantum dots;

a condenser optical system for collecting light emitted from said quantum dots;

an observation optical system for observing the light emitted from said quantum dots with a naked eye; and an image pickup optical system for detecting the light emitted from said quantum dots to perform imaging;

wherein said illumination optical system includes:

a variable long-pass filter unit in which a cut-off wavelength for determining a lower limit of a wavelength band of said excitation light to be applied to said quantum dots is variable; and a variable excitation filter formed from a short-pass filter in which a cut-off wavelength for determining an upper limit of the wavelength band of said excitation light to be applied to said quantum dots is variable;

said observation optical system including a barrier filter formed from a short-cut filter for cutting off the excitation light;

said image pickup optical system including a plurality of filter devices different in transmission wavelength band and capable of setting a plurality of different transmission wavelength bands.

* * * * *